(12) United States Patent
Nayeri et al.

(10) Patent No.: US 9,435,815 B2
(45) Date of Patent: Sep. 6, 2016

(54) METHOD FOR RAPID DETECTION OF HEPATOCYTE GROWTH FACTOR IN BIOLOGICAL FLUIDS

(71) Applicant: PEAS Institut AB, Linköping (SE)

(72) Inventors: Fariba Nayeri, Linköping (SE); Kamal Bahar, Tehran (IR)

(73) Assignee: PEAS INSTITUT AB, Linkoping (SE)

( * ) Notice: Subject to any disclaimer, the term of this patent is extended or adjusted under 35 U.S.C. 154(b) by 0 days.

(21) Appl. No.: 14/380,153

(22) PCT Filed: Feb. 22, 2013

(86) PCT No.: PCT/SE2013/050157
§ 371 (c)(1),
(2) Date: Aug. 21, 2014

(87) PCT Pub. No.: WO2013/126013
PCT Pub. Date: Aug. 29, 2013

(65) Prior Publication Data
US 2015/0037908 A1    Feb. 5, 2015

(30) Foreign Application Priority Data
Feb. 22, 2012    (SE) ...................................... 1250158

(51) Int. Cl.
*G01N 33/74*    (2006.01)
*G01N 33/52*    (2006.01)

(52) U.S. Cl.
CPC .............. *G01N 33/74* (2013.01); *G01N 33/52* (2013.01); *G01N 2333/4753* (2013.01)

(58) Field of Classification Search
CPC .................................................... G01N 33/74
See application file for complete search history.

(56) References Cited

U.S. PATENT DOCUMENTS 5,183,742 A * 2/1993 Omoto et al. .................. 435/14

FOREIGN PATENT DOCUMENTS

| WO | 0217964 A1 | 3/2002 |
|---|---|---|
| WO | 2005031365 A2 | 4/2005 |
| WO | 2010151222 A1 | 12/2010 |

OTHER PUBLICATIONS

Bourdoux et al., "Electrophoresis Cellulose Acetate vs Agarose Gel, Visual Inspection v Densitometry," Clinical Chemistry vol. 27, No. 11 (1981).*
Catlow et al. "Hepatocyte growth factor/scatter factor and its interaction with heparan sulphate and dermatan sulphate" Biochem Soc Trans. Apr. 2003;31(2):352-3.*

(Continued)

*Primary Examiner* — Shafiqul Haq
*Assistant Examiner* — Nam Nguyen
(74) *Attorney, Agent, or Firm* — Browdy and Neimark, P.L.L.C.

(57) ABSTRACT

The present invention relates to a method for determining the presence, absence or amount of biologically active HGF in a sample, comprising the steps (i) bringing the sample in contact with a first porous solid phase comprising a HGF binding component of the extracellular matrix or cell membrane, and an indicator composition comprising bromothymol blue and a quaternary ammonium compound; and (ii) correlating the color of the porous solid phase with the presence, absence or amount of biologically active HGF in the sample. It further relates to a device comprising a first porous solid phase comprising at least one HGF-binding component of the extracellular matrix or cell membrane, and an indicator composition comprising bromothymol blue and a quaternary ammonium compound.

4 Claims, 1 Drawing Sheet

(56) References Cited

OTHER PUBLICATIONS

Nakka, et al., A methachromatic-based experimental model for identification of bowel as the focus of an acute inflammation, Open Journal of Gastroenterology, 2013, pp. 42-48, vol. 3.

Nayeri, et al., Clinical impact of real-time evaluation of the biological activity and degradation of hepatocyte growth factor, Growth Factors, Jun. 2008, pp. 163-171, vol. 26(3).
European Extended Search Report for application No. 13 75 1847, search completion date Jun. 30, 2015., mail date Jul. 17, 2015).

* cited by examiner

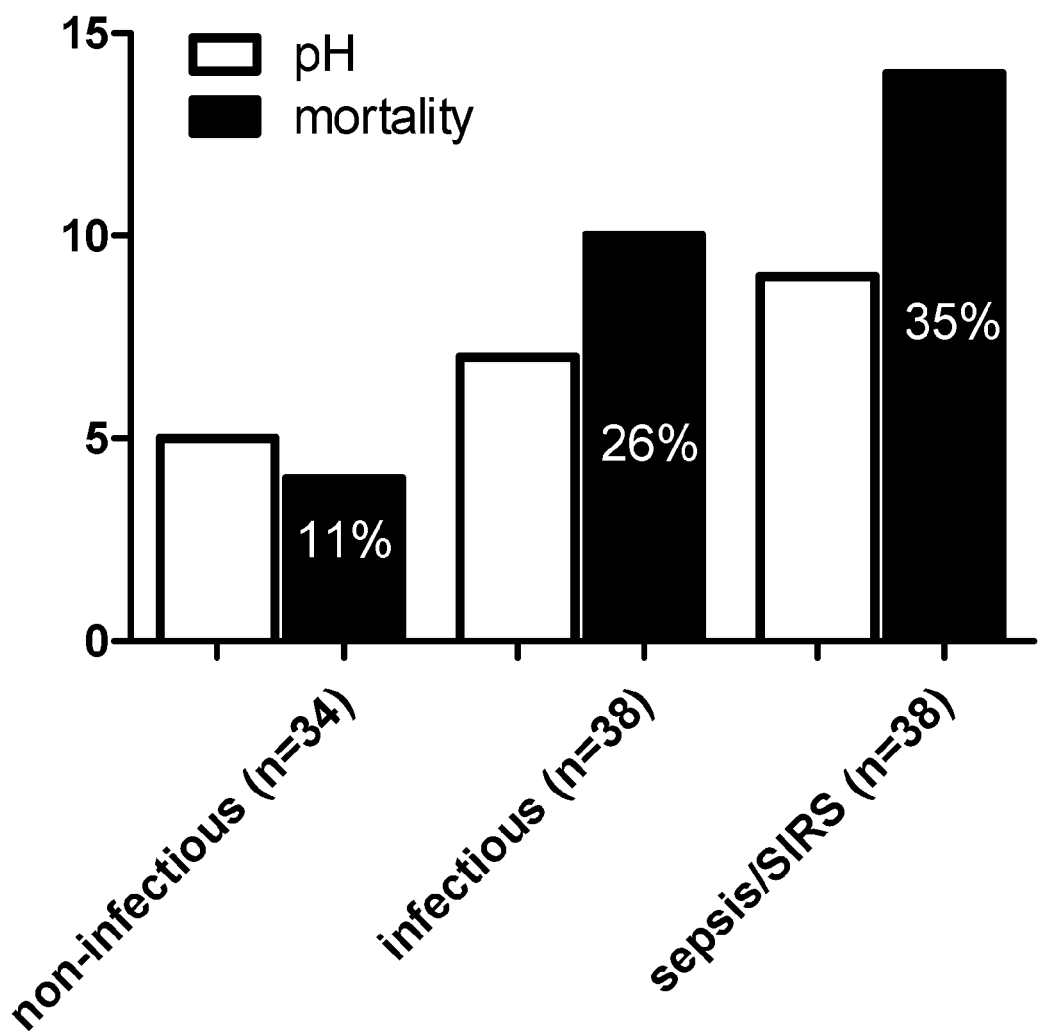

METHOD FOR RAPID DETECTION OF HEPATOCYTE GROWTH FACTOR IN BIOLOGICAL FLUIDS

FIELD OF THE INVENTION

The present invention is in the technical field of products for detecting presence of growth factors such as hepatocyte growth factor (HGF) in biological samples. It also relates to methods for performing such methods.

BACKGROUND OF THE INVENTION

Hepatocyte growth factor (HGF) is a unique growth factor, which is unrelated to other well-known polypeptide mitogens. It is a protein expressed in the mesenchymal cells such as lung macrophages and fibroblasts, Kupffer cells in the liver and leukocytes. HGF is secreted in response to cell damage and appears to be important for the regeneration of certain organs and healing of wounds. It is a heterodimer, having disulphide bonded heavy and light chains of approximately 60 and 30 kDa respectively, first synthesized as an inactive precursor. The precursor is cleaved to an active protein in the damaged organ by a specific activator. HGF acts paracrinally, i.e. it affects adjacent cells, as well as endocrinally, i.e. it has a long-distance. The target cells of HGF are fully developed epithelial cells. HGF is produced and is present in high concentrations at sites of organ damage.

The systemic and local production of HGF in various infectious diseases has been studied and high serum HGF concentrations have been observed during acute infectious diseases such as gastroenteritis, sepsis, pneumonia, skin and soft tissue infections and pyelonephritis. Simultaneous with enhanced systemic production of HGF, high HGF concentrations have been found in cerebrospinal fluid during meningitis. Raised HGF concentrations in exhaled breath condensate in patients with pneumonia, which had no correlation to serum levels of HGF, indicated a local production of HGF during pneumonia. Furthermore the stability of HGF in serum has been studied and HGF was found to be very stable in diluted feces samples and several freeze-thaw cycles, different buffers or several years of storage at □20□C did not affect feces HGF concentrations significantly. High amounts of HGF in feces during diarrhea have been shown to possibly indicate that patient suffers from a transmittable gastroenteritis. Further, monitoring of HGF levels before and after treatment during infectious diseases has been shown to possibly reveal therapeutic failure at an early stage.

Recognizing the clinical importance and differences between recommended therapies, differential diagnosis between inflammatory disorders in the body has been the subject of several investigations. One major clinical problem is determining whether infection or other inflammatory disorders cause the disease. There are several markers that typically are used by physician to establish the right diagnosis such as microscopic analysis and culture of body fluids, white blood cell count, C-reactive protein, plasma procalcitonin and lactate. However, there are still no golden standards to be used. Problems in establishing correct diagnosis occurs daily while treating inflammatory disorders in bowel, ulcers, joint diseases, CNS disorders, peritoneal, pleural and pericardial effusions, among others. The amounts of routine markers such as CRP and WBC might be high in several disorders and cultures are not always positive in spite of an infection. High amounts of HGF and its application in diagnosis and prognosis of infectious diseases are discussed in PCT application PCT/SE2001/001831. Yet in these studies, the whole amount of HGF in the body fluids was determined by ELISA method. Various studies about HGF have been reported. Some studies have used determination of HGF in plasma/serum and urine for diagnosis and screening of diseases such as acute renal deficiency, myocardial infarction, carcinoma of bladder, acute pancreatitis and acute and chronic lung diseases. For this reason, previously described methods such as ELISA and Western blotting have been used. Detection of high amounts of cytokines during inflammatory diseases is not a unique finding. However, in some cases, determination of HGF has been found to be a sensitive method that could detect specific clinical problems much easier than the routine methods (PCT application PCT/SE2001/001831).

Previously described methods such as ELISA and Western blotting are based on an interaction between HGF in the samples and an antibody that binds specifically to HGF. In ELISA, the amount of HGF single-chain and double-chain is determined. By Western-blotting the quality of HGF in the body fluid is determined by detection of apparent molecular masses present in the sample. However the methods are cumbersome and laborious.

The innovative use of biosensors is useful, inexpensive and rapid in this area of analysis. Surface plasmon resonance (BIACORE®) method can be used for the detection of HGF in feces (WO2005/031365). The technique is able to detect HGF levels and quality in a single run.

WO2010/151222 describes a method for determining the presence, absence or amount of biologically active or inactive HGF in a sample, comprising bringing the sample in contact with a gel comprising a HGF binding component of the extracellular matrix or cell membrane, adding toluidine blue to the gel, and correlating the colour of the gel and/or a liquid in contact with the gel with the presence, absence or amount of biologically active HGF in the sample.

In the Case of Infection:

In different organs, the levels of HGF are increased locally at the site of infection. The whole amount of protein might be detected by ELISA. Using Biacore technology, detection of the level of interaction (signals) to monoclonal, polyclonal antibodies to HGF as well as heparan sulphate proteoglycan (HSPG) immobilized to the chip, is high and it correlates positively to the results obtained by ELISA.

In the Case of Chronic Inflammation:

In spite of high amounts of HGF in samples that might be found by ELISA, non-significant correlation between ELISA and the results obtained by Biacore is observed. It might be no or very low signals detected by Biacore that shows a weak interaction to the ligands. The interaction to c-met protooncogene receptor might be high and the signals correlate positively to the level of immobilization. There is low signal rate at the HSPG channel. Adding HSPG or dextran sulphate to the samples at least 10 minutes prior to analysis might not diminish the signal at the HSPG channel. The protein might be biologically inactive.

Method (Platform)

Underlying Mechanism

The growth factors and cytokines such as Hepatocyte growth factor produced during injuries are released endocrinally and produced locally by the neighbor mesenchymal cells. The protein interacts with the high affinity cell binding specific receptor and sends signal into the cell resulting in regeneration of injured organ. In the case of HGF a non-specific receptor on the cell membrane and extracellular matrix (ECM) is needed to capture the cytokine and make it available to the specific receptor (c-Met receptor). Therefore the variants of HGF which show no affinity to HSPG or other proteoaminoglycans are not captured by ECM after release and might not interact with the specific receptor. Thus the protein might act as inactive in spite of high affinity to c-Met receptor.

In our previous works we have studied HGF by SDS-page, Western blot, ELISA and SPR and shown that the HGF protein (endogenous or recombinant) which did not bind to proteoaminoglycan (HSPG, heparan sulphate) or dextran sulphate, had no biological effect in the in-vivo (hair growth mice) or in-vitro biological activity methods (CCL-53.1 cells) used in our group. We have seen differences in patients with acute infection compared to chronic inflammation in binding affinity to HSPG in SPR method. Our primary conclusion is that in patients with chronic inflammation the high hierarchy cytokines such as HGF are inactivated and therefore they might need exogenous biologically active HGF to stimulate regeneration. As an example treatment with exogenic HGF has been shown to be beneficial in treatment of some cases of chronic leg ulcers (PCT application PCT/SE2001/001831). HGF has been found to enhance migration of healthy neighbor skin epithelial cells towards the damaged area by changing the cytoskletal structure of cells in vitro. An enhanced expression of met proto-oncogene receptor (c-met) in the ulcer area of patients with chronic ulcers is seen. Treatment with exogenous HGF decreased c-met expression significantly. There was a negative correlation between biologically active endogenous HGF concentration in secretion from the ulcers and met proto-oncogene receptor (c-met) expression. Treatments with exogenous HGF in the patients with a low amount of endogenous HGF and high met proto-oncogene receptor (c-met) expression caused vascular proliferation and ulcer area reduction. This model of organ injury in the skin and the related events might be true in other organ tissues as well.

SUMMARY OF THE INVENTION

In a first aspect the present invention relates to a method for detecting presence or absence of biologically active HGF in a sample, comprising bringing a HGF containing sample in contact with a porous solid phase having immobilised therein at least one HGF-binding component of the extracellular matrix (ECM) or cell membrane, such as a proteoaminoglycan or a glucosaminoglycan, and an indicator composition comprising bromothymol blue and a quaternary ammonium compound.

In a second aspect, the present invention relates to a device comprising a porous solid phase having immobilised therein at least one HGF-binding component of the extracellular matrix (ECM) or cell membrane, such as a proteoaminoglycan or a glucosaminoglycan, and an indicator composition comprising bromothymol blue and a quaternary ammonium compound.

BRIEF DESCRIPTION OF THE FIGURES

FIG. 1: Histogram showing increasing mortality rate according to feces pH

DEFINITIONS AND ABBREVIATIONS

The quality of HGF indicates the ability of HGF to bind to the extracellular matrix and exert its biological effects in vivo.

HGF means Hepatocyte Growth factor, also called Scatter Factor.

ECM means extracellular matrix.

HSPG means heparan sulphate proteoglycan.

MQ, or Milli-Q, refers to water that has been purified and deionized to a high degree.

PBS refers to phosphate buffer saline.

DETAILED DESCRIPTION OF THE INVENTION

Hepatocyte Growth Factor in its biologically active form has high affinity to proteoaminoglycans such as heparan sulphate proteoglycan (HSPG) and dextran sulphate. This affinity resembles the binding of growth factor to the cell membrane prior to interaction to its membrane-binding receptor.

This affinity is utilized in the following aspects and embodiments of the present invention. Based on the previous results using the observations from SPR method that showed that cytokines with high affinity to ECM components were released during acute infection, the inventors have prepared a platform by addition of amounts of proteoaminoglycan in a base solid matrix, such as cellulose. The affinity of protein to proteoaminoglycan is then visualized by colour changes in the presence of indicators including bromothymol blue a quaternary ammonium compound and/or methyl red.

The invention uses a pad phase containing a HGF binding component of the extracellular matrix or cell membrane, preferably dextran sulphate or HSPG. The pad is made of a porous solid phase, such as cellulose, nitrocellulose or paper. A presently preferred porous solid phase is a thick cellulose based filter paper with high loading capacity and medium retention filter paper 598 Schleicher & Schull. The following recipe is presently preferred:

The porous solid phase is impregnated with a solution containing 0.4% Quaternary ammonium compound (Merck) and 0.1% bromothymol blue (Panreac) in methanol. All chemicals are fixed to cellulose matrix by adding 0.5% coating stabilizer (Acros). The solid phase is dried in a current of warm air.

Next, the porous solid phase is soaked for 5 to 10 seconds with a solution composed of 0.1 mM of Dextran sulphate (Fluka) in deionized distilled water (MQ) and dried in a current of warm air.

In one embodiment, a second solid phase for use as a pH indicator is also prepared. The second solid porous solid phase is impregnated with a solution containing 0.02% methyl red (Merck), 0.4% Quaternary ammonium compound (Merck) and 0.1% bromothymol blue (Panreac) in methanol. All chemicals are fixed to cellulose matrix by adding 0.5% coating stabilizer (Acros). The second solid phase is dried in a current of warm air. This second solid porous phase preferably does not contain a HGF binding component of the extracellular matrix or cell membrane.

The first porous solid phase comprising proteoaminoglycan with indicator composition, and optionally the second porous solid phase for use as a pH indicator, might be fixed on two sided adhesive paper and immobilized on a solid support, such as a plastic band, later and cut into strips of suitable size for use, such as with a width of 6 mm.

In practice, for ease of performance, a loopful brush of faeces is transferred into 0.5 ml of dilution buffer (0.1 M of PBS pH 7.4) or water (preferably MQ) and a test strip comprising a porous solid phase immobilized on a solid support is dipped into the solution. When test strips are dipped into solutions containing HGF, depending upon the amount of analyte, HGF specifically react with its conjugate or receptor e.g. dextran sulphate, therefore the color of strip changes from yellow to various observable intensity of green to navy blue color.

The other components of extracellular matrix (glucosaminoglycans) might be used as well but Dextran sulphate is cheaper in price and shows similar results.

The invention relates to a method comprising dipping of a strip into a biological sample or diluted by buffer, preferably PBS 0.5 M to 0.15 M, pH 6.00-8.00, or water (preferably MQ) whereby biologically active HGF attaches to dextran sulphate.

Remaining drops of sample on the edge of strip is removed by tapping on tissue paper. Interaction between dextran sulphate and indicator changes the colour of the pad from yellow to spectrum of green colour to dark blue as positive signals for presence of HGF.

There is a specific interaction between biologically active HGF and dextran sulphate in the presence of indicators in the porous solid phase medium. Since the sample contains biologically active HGF that binds to dextran sulphate, the colour of the porous solid phase changes.

The intensity of green colour depends on the affinity of HGF to dextran sulphate and blocking H+ ion in the porous solid phase.

The amount of HGF, in observed green colour intensity in porous solid phase, could be determined by a comparative measurement of HGF using a standard method, e.g. a quantitative ELISA method. Optionally, one or more reference solutions of known HGF content are used to evaluate the reaction result. A negative reference may be used (e.g. water or PBS). A positive reference may be a healthy body fluid sample or a HGF containing product, with known HGF content.

For analysis of some samples, such as excrement including urine and faeces, it may be of interest to analyse the pH of the sample in addition to presence, absence or amount of biologically active HGF. A second porous solid phase for use as a pH indicator, as described above, are thus preferably introduced in methods and devices for use with such samples By the method of the invention it is possible to rapidly distinguish an acute inflammation such as bacterial infection in organ from a chronic inflammation.

The methods and products according to the invention may be used to analyse the following:
- Differences between septic arthritis and non-septic or reactive arthritis in joints
- Differences between acute transmittable gastroenteritis and chronic inflammatory bowel diseases or other causes of diarrhea
- Differences between acute septic meningitis and non-specific pleocytosis in cerebrospinal fluid
- Differences between acute renal insufficiency as well as pyelonephritis and distal urinary tract infection as well as chronic renal injury
- Differences between pneumonia and chronic obstructive lung disease in exhaled breath condensate
- Differences between septic inflammation in pleural effusion and ascites and non-septic inflammation
- Presence of HGF in serum and plasma
- Presence of HGF in saliva
- Standard evaluation of biologically active HGF in medications and blood products.
- Monitoring of antibiotic treatment.
- Locate the infectious focus during disease

Examples

A strip test with two surfaces for detection of binding affinity to HSPG and pH was developed in accordance with the present invention. In this example the strip test has been evaluated for identification of infectious gastroenteritis from other causes of diarrhea. The correlation of fecal pH to survival in a group patient with SIRS and the correlation of results of test to fecal calprotectin in detection of serious chronic inflammatory diseases have been assessed. The sensitivity of routine microbiological procedures to identify an infectious gastroenteritis was assessed retrospectively in a patient material admitted and dismissed in 2011 to our ward.

Study Population

The feces samples of all of the patients that searched the health facilities because of bowel disturbances in Östergötland, Sweden, were included in the study. There were no exclusion criteria. The samples were coded at once and unidentified. Between 3rd Mar. and 3 Aug. 2012 Total 445 feces samples (10-99, median 70 years, 243 female) from patients that searched the health care centers (n=140) or were admitted to the University Hospital in Linkoping, County hospitals in Norrköping and Motala (n=305), were analyzed consecutively with the Strip test within 48 hours after collection before the culture or PCR results were available. The Physician in charge in each ward conducted the diagnosis procedure and treatment. Therefore the reference tests were performed accordingly on patients. Further twenty-seven culture negative feces samples (also included in the previous study) from healthy volunteers (9-73, median 53 years, 17 women) were included. Further 64 feces samples collected 2003 (n=16), 2009 (n=20) and 2011 (n=28) with verified infection, that were kept frozen at −20° C. were re-thawed and analyzed retrospectively. Total 85 samples from patients with chronic diarrhea, sent from health centers to the Department of Biochemistry in 2011 for semi-quantitative fecal calprotectin test and had been kept frozen at −20° C. since, were re-thawed and analyzed.

The project leader studied the patient-journals and the result of strip test and the medical history were documented. The files were updated daily and the results of routine tests, x-rays, endoscopic procedures and final diagnosis before patient was dismissed were documented consequently. The patients were followed up to one year after inclusion for ultimate diagnosis and outcome. The feces samples of volunteers without diarrhea were included in the study unidentified. The Ethical Committee in Linkoping approved the study protocol.

Assay Accomplishment and Interpretation of Results

Feces were stored in room temperature for 15 minutes prior to analysis. The enclosed micro-brush is soaked in Milli Q water and then immersed in feces for 10 seconds, The micro-brush is then wiped on the strip pads and the color change is observed within 60 seconds and compared to the CMYK color chart (Klasner et al., Anal Bioanl Chem, 2010, July; 397 (5) 1821-1829).

The Reproducibility of Strip Test

In order to control method variability in preparation, 10 samples were analyzed 10 times with the different batches. Twenty strips from each batch were also tested with negative and positive controls. Positive and negative controls were also used prior to analysis of samples daily. Feces samples were analyzed in duplicates.

Reference Tests

Stool examinations by means of a combination of microscopic (n=52), viral (Calicivirus PCR, Rotavirus and Adenovirus antigen detection with ELISA, n=90) and bacterial culture methods (n=170) as well as serological and toxin-identification techniques (*Clostridium difficile* toxin, n=431), method for detection of semi-quantitative calprotectin (n=85 was performed on fresh feces samples collected 2011) and feces haemoglobin (n=30) were performed as routine tests at the University Hospital in Linköping. A variety of X-ray and endoscopic techniques were utilized as indicated. The strip test was performed on all feces sample. However, the results of strip test were observed and documented before the results of reference tests were available.

External Validation

In order to do an objective evaluation of test the results of the strip test performed on fresh stool of patients that were admitted to the Department of Infectious Diseases in Linköping, were documented immediately in both research database as well as digital patient journal (COSMIC) and signed by date and time. An external reviewer studied the test results and ultimate outcome to evaluate the sensitivity of test in cases (n=30).

Retrospective Study of Cases with Diagnose Infectious Gastroenteritis 2011

In 181 patients that were admitted to the Department of Infectious Diseases in Linköping in 2011 and were dismissed under diagnosis infectious gastroenteritis, the medical journal was studied retrospectively and the sensitivity of total conventional microbiological test assessed in 2012 (Table 3). A total of 187 feces cultures for *Salmonella, Shigella* and *Campylobacter*, 7 feces cultures for *Clostridium* typing, 23 feces cultures for EHEC, 123 Calici virus PCR and 105 Rotavirus+Enterovirus ELISA and 51 parasitological analysis of feces were undertaken.

Statistics

Regression analysis was performed for correlations using Graphpad prism version 5. Specificity (number of true negative/number of true negative+number of false positive), Sensitivity (number of true positive/number of true positive+number of false negative), Positive Predictive Value (PPV=True positive/true positive+false positive), Negative Predictive Value (NPV=True negative/true negative+false negative) and Accuracy (True positive+true negative/true positive+true negative+false positive+false negative) of the test results were calculated. Kruskal-Wallis, Mann-Whitney, and Fischer's exact test were used for feces pH and mortality and binary logistic regression Minitab 16 was used for comparisons between strip test and semi-quantitative feces calprotectin test.

Results

Sub-Groups

Infectious gastroenteritis: Totally in 173 cases the stool examinations revealed positive cultures (*Salmonella* n=6, *Campylobacter* n=15 and *Clostridium difficile* n=113), viral diagnosis (Calici virus n=23, Rota virus n=12 and Adenovirus n=1) parasites (*Schistosomia mansoni* n=1 and *Blastocystis homonis* n=3). In 34 cases *Clostridium difficile* infection was highly suspected but not culture verified. The patients were efficiently treated with medication directed to *Clostridium difficile* infection. Thus sub-group with infectious gastroenteritis composed of 207 feces samples (Table 1). The Strip test was negative in 9 out of 133 cases of bacterial infection (6.7%). The frequency of false negative results was higher in viral gastroenteritis (6 out of 36 cases=16%). The review of medical history revealed that no false negative results were seen in the cases with viral gastroenteritis where the samples were collected within the first 2 days of onset of diarrhea. In 9 cases in which the acute symptom of diarrhea had resolved but the routine tests revealed positive results, the strip test was negative. This group has been considered as carriers and omitted from statistic calculations.

Non-infectious cases: In 172 cases bowel as focus of infection was ruled out. This group is consisted of the cases in which the routine tests were negative and diarrhea was considered as a bi-symptom in the course of other diseases (n=123) or IBD (n=36). Totally in 199 cases in this sub-group (including healthy volunteers n=27), the strip test was positive in 13 cases (Table 1).

SIRS: Diarrhea during the course of sepsis with multiple organ dysfunction and/or SIRS was observed in 40 cases. In this group generalized inflammation and organ dysfunction was suspected.

Suspicious infection/undefined: In 81 patients, routine tests did not reveal infection. The medical history and/or the diagnostic procedure were incomplete or not available and therefore it was not possible to define the cause of diarrhea. However, infectious gastroenteritis was suspected in cases with the epidemiological history of infection or previous cultures. This group is not included in statistical analysis because the diagnosis was not objectively verified.

Estimates

Sensitivity, specificity, positive predictive value and negative predictive value as well as accuracy were calculated in groups with verified infectious gastroenteritis (n=207) and non-infectious cases which in turn included patients with IBD, patient with other systemic diseases and healthy (n=199). As shown in Table 2, Strip test could distinguish acute infectious gastroenteritis with a sensitivity of 92.2% and specificity 93.5% and a positive predictive value 93.6% and negative predictive value 92.1%. The accuracy of test was 92.9%.

pH impact in mortality was calculated in three groups consisted of infectious gastroenteritis (n=38), non-infectious diarrhea (n=34) and sepsis/SIRS (n=38). The feces pH was tested by strip test and documented using color chart scale. The pH and mortality was significant higher in the group sepsis/SIRS compared to non-infectious gastroenteritis (P<0.05) (Kruskal-Wallis, Mann-Whitney, and Fischer's exact test were used for statistical analysis) (FIG. 1).

Correlation between the strip test and fecal calprotectin results were assessed in 85 cases with bowel disturbances seeking to the health care centers. None of these cases suffered from acute gastroenteritis and the results of routine test were negative. The medical history was checked after one year to investigate the outcome. In this selected material with chronic bowel disturbance, fecal calprotectin showed a significant correlation to severe bowel disease (binary logistic regression Minitab 16 p<0.01) with a high negative predictive value (NPV=0.92) that did not differ when both feces calprotectin and Dexact-f were controlled in the same material. Simultaneous control of feces calprotectin and Dexact-f could distinguish the severe chronic bowel disease from the benign ones in 14/19 cases before the diagnostic procedures (CT scan, colposcopy and pathologic diagnostic) revealed the nature of disturbance. Thus positive Dexact-f has an impact in diagnosis of acute inflammation in bowel and negative feces calprotectin an impact to rule out chronic inflammation (Table 2).

No significant correlation was found between results of strip test and presence of blood in feces ($R^2$=0.08).

No significant differences between analysis of samples with strip tests from same or different batches were observed.

The sensitivity of the routine microbiological diagnostic methods to identify the infectious gastroenteritis was 59% in the material from 2011. Study of the journals and ultimate outcome revealed that risk for wrong diagnosis and over consumption of antibiotics was least in Rotavirus gastroenteritis. The most antibiotic over consumption happened in the middle age patients 40-70 years and especially in the group with bacterial gastroenteritis. Double-infection was seen in 4 cases and one case of parasite infection (Giardia) was observed.

Discussion

Determination of feces pH gives important information about the ion exchange in bowel (Bachmann O, et al. *Acta Physiol* (*Oxf*). 2011 January; 201 (1):33-46). This information has been used as a non-specific method for diagnosis of some bowel infections. Recently this method has been presented to predict the outcome in severely ill patients (Osuka A et al. *Crit Care*. 2012 Jul. 10; 16 (4):R119.). Due to the fact that patients with generalized inflammatory response; SIRS in the course of severe trauma and/or sepsis had high production of HGF in bowel and high pH in feces (accepted manuscript), we had hypothesized that simultaneous examination of HGF and pH in feces might increase the sensitivity of strip test in diagnose of acute inflammation in bowel. We observed that patients with infectious gastroenteritis had higher pH compared to non-infectious cases and healthy. However, feces pH>8.0 was seen in cases with severe colitis and SIRS which in turn showed significant increased mortality. Thus a combination of positive strip test and pH<8.0 might indicate a self-limiting infectious gastroenteritis in need of fluid replacement. On the other hand, highly positive strip test with pH>8.0-9.0 might predict severe colitis septicemia or other severe illness in which empiric wide-range antibiotic treatment might be beneficial. This might result in less but more directed using of antibiotics.

Calprotectin is a protein expressed in bowel during inflammation. Presence of high calprotectin levels in feces indicates an inflammatory process. Although the test has a high negative predictive value, presence of calprotectin in feces cannot identify acute from chronic inflammatory bowel disease (Kostakis I D et al. *Dig Dis Sci*. 2012 Aug. 17. and J Chen C C et al., *Pediatr Gastroenterol Nutr*. 2012 Jun. 13). In a recent study we have shown that HGF was highly expressed at the site of acute inflammation in the bowel but not at the area with chronic inflammation (submitted manuscript) and high HGF levels in feces might indicate an acute inflammatory process in bowel, such as during infection. In an out-patient group with bowel disturbances feces calprotectin was determined on fresh samples. This selected material consisted of cases in which control of feces calprotectin was chosen based on previous documentation on indication for such test and as suspected no infectious gastroenteritis was found. This patient group was followed during one year and the ultimate outcome documented. Feces were tested semi-quantitatively on fresh material (accepted manuscript) as well as on the re-thawed feces by strip test. The results were in agreement with other studies confirmed the negative predictive value of feces calprotectin to rule-out the severe chronic bowel diseases. However, the combination of high feces calprotectin and negative strip test could identify 10 out of 11 cases of IBD and 3 out of 4 cases with colon cancer in our material consisting of 85 patients (Table 2).

HGF was quite stable in feces as shown in a previous study (Nayeri F, et al. *Scand J Clin Lab Invest*. 2004; 64(6):589-97). We observed that even the re-thawed samples might be used in the strip test. However, it was crucial to take samples from feces during the active phase of disease, though false negative results were observed in cases in which test was taken several days after symptom debut in viral gastroenteritis.

Tables

TABLE 1

Sensitivity: 191/207 = 0.9227, Specificity: 186/199 = 0.935, Positive Predictive value (PPV) = 191/204 = 0.936, Negative Predictive value (NPV) = 186/202 = 0.921, Accuracy = 186/207 + 199 = 0.929

| Test result | Infectious diarrhea | | | | | Non-infectious diarrhea | | | | |
|---|---|---|---|---|---|---|---|---|---|---|
| | Verified Infectious | | | Highly suspected | Total | Other | | | Total | |
| | bacteria | virus | parasites | infectious | subgroups | causes | healthy | IBD | subgroups | Total |
| Dexact-f+ | 124 | 30 | 4 | 33 | 191 | 12 | 0 | 1 | 13 | 204 |
| Dexact-f− | 9 | 6 | 0 | 1 | 16 | 123 | 27 | 36 | 186 | 202 |
| Total | 133 | 36 | 4 | 34 | | 135 | 27 | 37 | 199 | |

TABLE 2

Feces samples gathered May 2011 from patients seeking to the health care centers for bowel diseases and control of medical history August 2012 (n = 84). Feces cultures (n = 19) were negative and parasitological diagnosis (n = 17) did not reveal pathogenic parasites in faces.

| Patients with chronic bowel disturbance | Severe chronic inflammatory bowel disease (cancer/celiaki/IBD) | Acute inflammation (colitis, diverticulitis) | IBS/laktos intolerance/resolved symptom |
|---|---|---|---|
| Calprotectin >60 + Strip test neg | 14 | 0 | 10 |
| Calprotectin <60 + Strip test neg | 4 | 0 | 47 |
| Calprotectin >60 | 15 | 3 | 10 |
| Calprotectin <60 | 4 | 0 | 47 |
| Strip test neg | 18 | 0 | 57 |
| Strip test pos | 1 | 3 | 6* |
| total | 19 | 3 | 63 |

*Three cases of blastocystis humonis were found in this group.

TABLE 3

Retrospective analysis of medical history of patients that were isolated at the Department of Infectious Diseases in Linköping with diagnosis "infectious gastroenteritis" in 2011

|  | Total N = 181 | Calicivirus N = 18 | Rotavirus N = 13 | Bacteria N = 22 | *Clostridium* N = 51 | Unclear N = 76 |
|---|---|---|---|---|---|---|
| Age median(years) | 69 | 78 | 72 | 63 | 75 | 62 |
| Sex female/male | 89/92 | 8/10 | 6/7 | 8/13 | 24/27 | nd |
| Admitted (days) median | 4 | 6 | 3 | 4 | 7 | 3 |
| Given antibiotics (other than Metronidazole) not motivated/total cases | 38/181 | 4/18 | 1/13 | 9/22 | 10/51 | 15/76 |
|  | 70-100 Years 9/83 | 40-70 years 26/61 | 18-40 years 3/37 |  |  |  |

The invention claimed is:

1. A method for determining the presence, absence or amount of biologically active Hepatocyte Growth Factor (HGF) in a fecal sample of a subject and correlating said presence, absence or amount of HGF with an acute inflammation of the bowel in the subject, said method comprising the steps of:
   bringing the fecal sample in contact with a first and a second porous solid phase of a test strip, said first and second porous phases being fixed to a solid support, said first porous phase comprising at least one HGF binding component of the extracellular matrix or cell membrane, and an HGF indicator composition in contact with the HGF binding component, said HGF indicator composition comprising bromothymol blue and a quaternary ammonium compound, said second porous phase comprising a pH indicator composition fixed to said second porous phase, said pH indicator composition comprising bromothymol blue, a quaternary ammonium compound and methyl red; and
   correlating the colour of the first porous solid phase with the color of a reference solution containing a known quantity of biologically active HGF and thereby determining presence, absence or amount of biologically active HGF in the fecal sample and determining the pH of the fecal sample from said second solid phase, wherein the presence of an amount or biologically active HGF in said fecal sample is indicative of an acute inflammation of the bowel in the subject when the pH of said fecal sample is >8 and wherein said HGF binding component is heparin sulphate proteoglycan or dextran sulphate, wherein the fecal sample is a fluid.

2. The method according to claim 1, wherein the correlation of the colour of the porous solid phase with the presence, absence or amount of biologically active HGF in the sample includes comparing the colour of the porous solid phase with a porous solid phase that has been brought into contact with at least one reference solution of known HGF content.

3. A test strip comprising a solid support, a first porous solid phase fixed on solid support and a second porous solid phase fixed on said solid support, said first porous solid phase comprising at least one HGF-binding component of the extracellular matrix or cell membrane, wherein said component is heparan sulphate proteoglycan or dextran sulphate, and an HGF indicator composition in contact with said component, said HGF indicator composition comprising bromothymol blue and a quaternary ammonium compound, said second porous solid phase comprising a pH indicator composition, said pH indicator composition fixed to said second porous solid phase, said pH indicator composition comprising bromothymol blue, a quaternary ammonium compound and methyl red.

4. The test strip according to claim 3, wherein at least one of said first and second porous solid phases comprises cellulose.

* * * * *